(12) United States Patent
Brand (10) Patent No.: US 9,927,521 B2
(45) Date of Patent: Mar. 27, 2018

(54) HIGH FREQUENCY ACOUSTIC SPECTRUM IMAGING METHOD AND DEVICE

(71) Applicant: SIEMENS AKTIENGESELLSCHAFT, Munich (DE)

(72) Inventor: Bastiaan Brand, HM Hilversum (NL)

(73) Assignee: Siemens Aktiengesellschaft, Munich (DE)

(*) Notice: Subject to any disclaimer, the term of this patent is extended or adjusted under 35 U.S.C. 154(b) by 420 days.

(21) Appl. No.: 14/803,174

(22) Filed: Jul. 20, 2015

(65) Prior Publication Data

US 2016/0018519 A1    Jan. 21, 2016

(30) Foreign Application Priority Data

Jul. 18, 2014  (EP) .................................. 14177581

(51) Int. Cl.
  *G01S 15/89*  (2006.01)
  *G01S 15/02*  (2006.01)
  (Continued)

(52) U.S. Cl.
  CPC .......... *G01S 15/89* (2013.01); *G01N 29/0609* (2013.01); *G01N 29/0654* (2013.01); *G01N 29/12* (2013.01); *G01N 29/14* (2013.01); *G01S 3/801* (2013.01); *G01S 3/802* (2013.01); *G01S 3/84* (2013.01); *G01S 7/6263* (2013.01);
  (Continued)

(58) Field of Classification Search
  CPC ........ G01S 3/801; G01S 7/6263; G01S 15/89; G01S 3/84; G01S 15/025; G01S 3/802; G01N 29/14; G01N 29/0609; G01N 29/12; G01N 2291/2697; H04R 1/342
  See application file for complete search history.

(56) References Cited

U.S. PATENT DOCUMENTS 4,006,444 A    2/1977  Quate et al.
5,435,312 A    7/1995  Spivey et al.
      (Continued)

FOREIGN PATENT DOCUMENTS

DE    102012019458 A1    4/2014
EP         2697699 A1    2/2014
      (Continued)

*Primary Examiner* — Daniel Pihulic
(74) *Attorney, Agent, or Firm* — Laurence Greenberg; Werner Stemer; Ralph Locher (57) ABSTRACT

A method and a device for high frequency acoustic spectrum imaging for an object over a field of view. A camera captures an image of the object. A raster with grids is created as an overlay on the captured image. A directional microphone detects high frequency acoustic waves emanating from the object. An acoustic data signal corresponding to the high frequency acoustic waves is generated by a microphone data processing unit. The coordinates of the focal point of the directional microphone on the grid of the raster is recorded and sent as a real-time feedback position signal to a processor for each measurement of the acoustic signal data. The processor plots a visual representation of the acoustic signal data mapping it to the corresponding coordinates on the raster and creates a high frequency acoustic spectrum image for the object by superimposing the raster on the captured image.

16 Claims, 3 Drawing Sheets

(51) Int. Cl.
*G01S 7/62* (2006.01)
*G01N 29/06* (2006.01)
*G01N 29/12* (2006.01)
*G01N 29/14* (2006.01)
*G01S 3/802* (2006.01)
*G01S 3/801* (2006.01)
*G01S 3/84* (2006.01)
*H04R 1/34* (2006.01)

(52) U.S. Cl.
CPC .... *G01S 15/025* (2013.01); *G01N 2291/2697* (2013.01); *H04R 1/342* (2013.01)

(56) References Cited

U.S. PATENT DOCUMENTS

| | | |
|---|---|---|
| 2013/0142009 A1 | 6/2013 | Chang et al. |
| 2014/0025211 A1 | 1/2014 | Cheim et al. |
| 2014/0200837 A1 | 7/2014 | Blair et al. |
| 2014/0241548 A1 | 8/2014 | Kim et al. |
| 2016/0018519 A1* | 1/2016 | Brand .................... G01S 3/801 367/7 |

FOREIGN PATENT DOCUMENTS

| | | |
|---|---|---|
| EP | 2746737 A1 | 6/2014 |
| WO | 2012142355 A1 | 10/2012 |
| WO | 2013082480 A1 | 6/2013 |

\* cited by examiner

FIG 6

HIGH FREQUENCY ACOUSTIC SPECTRUM IMAGING METHOD AND DEVICE

CROSS-REFERENCE TO RELATED APPLICATION

This application claims the priority, under 35 U.S.C. § 119, of European patent application EP 14177581, filed Jul. 18, 2014; the prior application is herewith incorporated by reference in its entirety.

BACKGROUND OF THE INVENTION

Field of the Invention

The present invention relates in general to acoustic spectrum imaging methods and more particularly concerns methods and devices for high frequency acoustic spectrum imaging for an object.

With aging assets and increased demands for reliability and availability the maintenance philosophy for assets, especially medium and high voltage assets, is more and more shifting towards predictive health management or reliability-centered asset management techniques. The different techniques however rely, for a great part, on indices that are set on assumptions. All information that can be collected during the 'in service' period for an asset is of great value as long as it is being used as efficiently as possible during the 'maintenance window' for an asset. This often requires proper planning and demands for 'non intrusive' inspection technologies that can be repeated with the smallest possible fault margin. It is also necessary that the collected data must be in a format that can be quantified including a relationship to the origin and location of the individual data points.

A variety of technologies are being used in the field to inspect the assets or equipments for deviations from normal in data with respect to similar or adjacent assets of the same type or if compared to diagnostics performed in an earlier stage.

One system for dynamic assessment, including risk of failure assessments, for high-voltage electrical components is described in US 2014/0025211 A1 and its counterpart international publication WO 2012/142355 A1 and European published patent application EP 2 697 699 A1. It discloses a dynamic assessment system for monitoring high-voltage electrical components, which includes a computer system that is configured to receive data from a plurality of on-line sensors configured to monitor various operating parameters, for example status of the cooling system, fans, pumps; transformer active part insulation test results; turns ratios, visual/audible inspection results etc., associated with the operation of a plurality of electrical components such as a plurality of electrical transformers. The computer system is configured to automatically and continuously correlate the data from the on-line sensors with data from various off-line databases and supervisory networks associated with monitoring the operation of the power distribution network, so as to generate dynamic operating condition assessments, including risk of failure assessments, of each of the monitored electrical components.

In many cases a general two or three level approach is used to prevent failures or accelerated aging, namely, a quick scan, often repeated on a yearly bases, a more in-depth monitoring session over a longer period of time and a root cause analysis once an unexpected reading is registered from one of the first two approaches. The cost relating to the levels and the impact on redundancy varies from light to severe in order from one to three. The technologies commonly used for level one and two are most often 'non-intrusive' techniques and implemented in IEC and IEEE standards, such as Digital Infrared Thermal Imaging (DITI), Partial Discharge (PD) surveys, Dissolved Gas Analyses (DGA), Gas density inspections (GDI), and some more, depending on the physical properties of the system, for example, insulating media and contact resistance in the case of medium and high voltage assets.

Reports often comprise a visual representation of the assets by means of pictures and the recorded data collected by the method of inspection. The inspection method might suffer from subjective errors if setting the indices for reliability is based on human hearing, personal interpretation and training of the investigator. The reports thus produced are highly skewed due to these human factors.

It has been observed that when a medium or a high voltage asset fails to perform it emanates high frequency acoustic waves, typically in the range of 30-50 kHz. However, there exists no known method for creation of a high frequency acoustic spectrum image using these high frequency waves and further predicting the health of an asset based on the high frequency acoustic spectrum image.

Creating acoustic image of objects by impinging the object externally with waves is already known. Patent application publication US 2013/0142009 A1 and its counterpart international publication WO 2013/082480 describe a method to perform acoustic imaging of an object. According to the method an acoustic wave is acquired at a detector, where the acoustic wave propagates from a target to the detector. The target is acoustically illuminated to provide the acoustic wave. A signal from the detector in response to acquiring the acoustic wave is processed in a model such that the processing implements a synthetic acoustic lens to generate an image of the target.

U.S. Pat. No. 4,006,444 discloses an acoustic imaging apparatus wherein a beam of high frequency acoustic energy is directed to the object to be imaged to create variations in the transmitted acoustic energy which variations are then detected by a plurality of small particles suspended in the beam path for motion in response to radiation pressure produced by the incident acoustic energy, thus providing a visible image with high contrast sensitivity and excellent image resolution.

U.S. Pat. No. 5,435,312 provides an acoustic imaging device which utilizes scattered acoustic wave information to produce an image. The system consists of an array of acoustic transducers which at least partially encircle a medium to be imaged. The medium is sequentially insonified by each transducer with an acoustic signal comprised of at least one discrete frequency. The acoustic signal scatters from the medium and is detected by the remaining transducers. A data set representing the phase and amplitude of each discrete frequency at each transducer is acquired and used by a computer to calculate an image of the medium. Images acquired and calculated at each identifiable discrete frequency are combined in various ways in order to improve the quality of the final image of the medium.

In all the above methods the object to be imaged is impinged with waves externally and the acoustic image is created based on the effect the object has on the waves targeted at it.

Currently used acoustic imaging technologies cannot be used effectively for high frequency image creation because they work with an array of microphones and require large data handling and significant amount of post processing. The signal processing required by the currently used acoustic camera technology is very intensive and needs powerful hardware and plenty of memory storage. Because of this, signal processing is frequently done after the recording of data, which can hinder or prevent the use of the camera in analyzing sounds that only occur occasionally or at varying locations. Moreover, the microphones used are not capable of registering in the high frequency range and other sources of acoustic energy adjacent to or in the path towards the object to be observed will create a blind spot if the corresponding amplitudes of the acoustic waves are higher than these from the object to be observed. Thus there is no known method for creating an acoustic image using high frequency waves emitted by an object.

SUMMARY OF THE INVENTION

It is accordingly an object of the invention to provide an imaging method which overcomes the above-mentioned and other disadvantages of the heretofore-known devices and methods of this general type and which provides a high frequency acoustic spectrum image for an object using the high frequency waves emitted by the object, such as a medium or a high voltage asset.

With the foregoing and other objects in view there is provided, in accordance with the invention, a method for high frequency acoustic spectrum imaging for an object over a field of view, the method comprising:
  capturing an image of the object in the field of view;
  creating a raster with grids as an overlay on the image;
  detecting high frequency acoustic waves emanating from the object with a directional microphone by scanning through the grids of the raster;
  generating an acoustic signal data corresponding to the high frequency acoustic waves detected while scanning;
  registering coordinates of focal point of the directional microphone on the grid corresponding to each measurement of the acoustic signal data;
  plotting a visual representation of the acoustic signal data on the raster corresponding to its coordinates on the grid;
  superimposing the raster on the captured image to get the high frequency acoustic spectrum image for the object.

In other words, the object of the invention is achieved by a method for high frequency acoustic spectrum imaging for an object over a field of view. The method comprises a step of capturing an image of the object in the field of view, a step of creating a raster with grids as an overlay on the image, a step of detecting high frequency acoustic waves emanating from the object by scanning an area within the image by moving a directional microphone through the grids of the raster, a step of measuring the high frequency acoustic waves and generating an acoustic signal data corresponding to the high frequency acoustic waves at each grid, a step of registering coordinates (x, y) of the focal point of the directional microphone corresponding to every measurement of the acoustic signal data at each grid, a step of plotting the coordinates (x, y) and the acoustic signal data on the raster and finally a step of superimposing the raster on the captured image to get the high frequency acoustic spectrum image for the object.

The term "raster" is used synonymously with the term "screen," as used in printing and display technology. Similarly, the term "rasterizing" is used as a synonym for "screening."

With this invention it is possible to plot the acoustic spectrum emanating from individual objects in the field of view over an image captured by a camera, thus creating an acoustic image of the world as we see it. The image is an ordinary photograph of the object along with its surrounding that falls in the field of view of the camera. The object can be a switch gear, a transformer or any other high or medium voltage asset. This method will find similarity with digital infrared thermal imaging but for the acoustic spectrum. Therefore, the novelty lies in capturing acoustic data with a reference position or coordinates (x, y) and combining this information with a visual representation of the area that is scanned with the directional microphone. A directional microphone is a special microphone that picks up sound from a certain direction, or a number of particular directions.

According to an aspect of the invention, the directional microphone is a parabolic microphone. Parabolic microphones are highly directional; a small beam in the direct line between the object and the operator is used to gather signals. These microphones can capture sound from a very small area, for example of the order of 2 to 5 $cm^2$. These microphones can determine the exact coordinates of the point from which the high frequency waves are beamed and can be detected by the microphone owing to its highly directional nature.

Therefore, during scanning the microphone picks up the high frequency wave beams and the can determine the coordinates (x, y) from where the beams are aimed at or beams are passing through. The acoustic data for that particular area, for example 1 to 2 $cm^2$ can be plotted on the grid of the raster that is superimposed on the image captured of the field of view of the person operating the microphone, which includes the image of the object. Thus an acoustic image is created. Because of the fact that the invention uses a parabolic microphone, a small beam in the direct line between the object and the operator is used to gather signals. The actual target location is precisely measured in the image.

Another advantage of using parabolic microphone is that the noise or disturbing acoustic location surrounding the object does not interfere with the detection of the high frequency acoustic waves emanating from the object due to the directional nature of the microphone. In other words, these microphones have the ability to hear beyond the "disturbing acoustic location" and selectively detect the high frequency waves under consideration, leaving out the neighboring noise signals.

According to another embodiment of the method the raster has a grid density equivalent to the diameter or circumference of the focal point of the directional microphone. The grid can also have a density which may be more or less than the diameter or circumference of the focal point of the directional microphone. However, best performance for detection and plotting of the high frequency waves on the raster is possible when the grid is having a density equal to the diameter or circumference or circumference of the focal point of the microphone. Grid density means the distance between two adjacent grids of the raster.

In one aspect of the invention the acoustic signal data comprises of amplitude of the high frequency acoustic wave, and/or main frequency of the high frequency acoustic wave. The information about amplitude and main frequency of the acoustic wave gives characteristic details for plotting the information on the raster. The amplitude information gives the strength or intensity of the acoustic wave emanating from the object and the main frequency information provides useful information as to whether the acoustic waves lie in the frequency range of interest.

In an embodiment of the invention the step of registering coordinates (x, y) further comprises a step of sending a real-time feedback position signal of the co-ordinates (x, y) to a processor. Real-time feedback position signal makes it possible to generate a more accurate acoustic image in a lesser time. Whilst scanning the area inside the image, the coordinates of the focus point of the directional microphone, or more particularly of the dish of the directional microphone, is registered by means of the direct feedback of the position coordinates (x, y) of the microphone corresponding to its movement on the grid. During scanning the microphone moves from one position to another on the grid and it is essential that the feedback at every position be quickly recorded. Therefore, at every position of the microphone on the grid there will be a corresponding acoustic signal data.

The processor to which the real-time feedback position signal is sent can be any processor capable of recording, storing and processing the information.

While scanning with the directional microphone if the focus point of the microphone moves in to a new grid position, the acoustic signal data, which comprises of the amplitude and the main frequency of the acoustic wave, is stored in the processor along with the grid position or the grid number with the corresponding coordinates (x, y). This information can be alternately stored in a database. The information stored in the processor is retrieved for creating the high frequency acoustic spectrum image.

According to one embodiment of the invention, a minimum and a maximum amplitude threshold of the high frequency acoustic signal is set in the processor. While scanning the area within the image the directional microphone records, at various instances, high frequency acoustic waves having varying amplitudes. Having a minimum and a maximum threshold for amplitude will help in identifying and distinguishing areas in the image that have high levels of high frequency acoustic waves and could indicate an area that may require special attention. Keeping thresholds will also help in better visualization when the high frequency acoustic spectrum image is finally created.

In a further embodiment, the high frequency acoustic spectrum image of the object further comprises a color-coded visual representation of the amplitude or the frequency of the acoustic signal data. To make the visual representation of the acoustic waves on the image, the color coding would help to demarcate and distinguish areas with difference in the amplitude or main frequency and the gradient can be effectively represented in the image for better interpretation of the image in respect of the strength or intensity of the acoustic waves in the field of view.

In a further embodiment of the method, when the amplitude of the high frequency acoustic wave received on the directional microphone is above the maximum amplitude threshold the high frequency acoustic spectrum image for the object visualizes a first colored area on the raster. Similarly, when the amplitude of the high frequency acoustic signal received on the directional microphone is below the minimum amplitude threshold the high frequency acoustic spectrum image for the object visualizes a second colored area on the raster.

The first colored area can be red where it signifies high levels of acoustic signals and would warn the user to pay attention. The second colored area can be blue to signify low levels of acoustic signal and indicate safe levels or no danger. Any other colors may also be used depending on the user's choice.

In an embodiment of the method, the color-coded visual representation is used for plotting an 'amplitude image' for the object, wherein the differentiation in amplitude is made visible in a different color. For example, when the amplitude is 10 dB or below it is represented by the color blue on the image and when the amplitude is 50 dB or above red it is represented by the color red on the image. Amplitude in-between both thresholds will be an equivalent mixture of red and blue where the percentage of red will increase with increasing dB.

Similarly, the color-coded visual representation can also be used for plotting a 'frequency image' with higher frequencies being shown in red and lower frequencies represented by the color blue.

In a further embodiment a user can choose to view the 'amplitude image' and an option is available to the user to view the corresponding 'frequency image' by providing an input by way of a button. Therefore, the user can choose either to see the frequency or with a press on the button the user can see the equivalent amplitude.

In yet another embodiment, the image can be flipped sideways, and the amplitude of the high frequency acoustic wave can be plotted in a bar-type chart and the raster on the image can be colored in relation to the equivalent frequency.

According to an embodiment of the invention the coordinates (x, y) are sensed using an analog movement sensor, a servomotor, a joystick or a method for tracking a laser. The coordinates are measured in real-time with great accuracy of position.

Using a laser removes the need to use hardware or sensors. When using a laser, the coordinates (x, y) on the raster will not be captured by way of feedback from sensors. Instead, to exactly identify the location from which the high frequency acoustic waves are emanating, or the location at which the focal point of the directional microphone captures or senses the high frequency acoustic beam coming from the object, a software will be configured to recognize a laser-dot via the camera, directly plotting the acoustic signal data in the raster. A transparent layer in front of the camera view would eliminate the need for hardware even more.

In a preferred embodiment the grid density of the raster is 2×2 cm. Having the grids on the raster closer to each other will ensure that the position of the microphone is measured accurately and with a very small margin of error. For a best mode embodiment, the grid density of the raster must be equal to the diameter or circumference of the focal point of the directional microphone or in other words the focal point of the dish of the directional microphone.

In the method of this invention the directional microphone has a working range between 2 to 20 m. A directional microphone with a larger working range may also be used if it provides a better response.

The above method of high frequency acoustic spectrum imaging for an object over a field of view can find application in detecting failing media and high voltage assets like switchgears and disconnectors, power line terminations, cable terminations, insulators, bushings, power transformers, rectifiers, busbar etc.

Thus, the disclosed method for creating the high frequency acoustic spectrum image for objects, such as medium and high voltage assets, can be used to predict the health of the medium and high voltage assets based on the high frequency acoustic waves or partial discharge emissions emitted by it.

When the main frequency of the high frequency acoustic signal lies in a range of 30 to 50 kHz, partial discharge emissions are detected from the object, i.e., from the medium or high voltage asset, and the asset might fail in the near future. This method provides ways for predictive health management and asset management. Once such partial discharge emissions are detected and a high frequency acoustic spectrum image is created the location of the failing object can be identified and corrective measures can be taken to repair the object and prevent it from failing in the near future.

With the above and other objects in view there is also provided, in accordance with the invention, a device for generating a high frequency acoustic spectrum image of an object, the device comprising:

a camera for taking an image of the object;
a directional microphone for receiving high frequency acoustic waves emanating from the object;
a microphone data processing unit connected to said microphone for generating an acoustic signal data corresponding to the high frequency acoustic waves;
a feedback unit connected to said microphone for sending to a processor a real-time feedback position signal of coordinates of a focal point of the directional microphone corresponding to the acoustic signal data;
said processor being configured for plotting a visual representation of the acoustic signal data mapped to the corresponding coordinates on a raster and superimposing the raster on the image to create the high frequency acoustic spectrum image for the object.

In other words, there is described, according to yet another embodiment of the invention, a device for creating a high frequency acoustic spectrum image for an object. The device comprises a camera for taking an image of the object, a directional microphone for receiving high frequency acoustic waves emanating from the object, a measuring unit for measuring an acoustic signal data corresponding to the high frequency acoustic waves, a feedback unit for sending to a processor a real-time feedback position signal of co-ordinates (x, y) of focal point of the directional microphone corresponding to the acoustic signal data and the processor for plotting the coordinates (x, y) and the acoustic signal data on a raster and superimposing the raster on the image to create the high frequency acoustic spectrum image for the object. The raster is prepared as an overlay on the image taken by the camera.

In an embodiment of the device the feedback unit comprises any one of an analog movement sensor, a servomotor, a joystick or a device for tracking a pointer/laser or software that calculates the coordinates of a pointer/laser in the in the feedback from a camera. Using one of these feedback methods ensures that the feedback of the coordinates (x, y) of the focal point of the directional microphone is sent in real-time without any delay. The microphone movement is sensed by the sensor present in the feedback unit and the coordinates (x, y) of the position of the microphone is recorded. For every measurement of the high frequency acoustic waves, there is a corresponding coordinates (x, y) of the position of the microphone and the acoustic signal data (d1).

In another embodiment the acoustic signal data comprises of an amplitude of the high frequency acoustic wave, or a main frequency of the high frequency acoustic wave or both. The acoustic signal data corresponds to each grid location of the raster. Information about the amplitude and the main frequency allows for better visual representation of the high frequency acoustic wave on the image.

According to yet another embodiment the object is any one but not limited to the following assets, switchgear, disconnector, power line termination, cable termination, insulator, bushing, power transformer, rectifier or a busbar. These medium and high voltage assets most often radiate high frequency acoustic signals before they begin to fail. The high frequency acoustic signals can be a cause of failure or a result of failure. In the case of high frequency acoustic signals as a result of failure other failure modes might be captured. Creating an acoustic spectrum image for these assets can help in preventive asset health management.

In another embodiment the high frequency acoustic spectrum image for the object further comprises a color-coded visual representation of the acoustic signal data signifying strength or intensity of the high frequency acoustic waves. By using a color-code, the high frequency acoustic spectrum image can be easily interpreted by a user and the information about the partial discharge emissions can be projected in a less complicated manner requiring lesser analysis of the image. By looking at the color-code the user can assess the strength of the high frequency acoustic waves and identify areas with higher than normal emissions which would require closer attention.

In a best mode embodiment of this device the spatial resolution of the image is 2 cm and the acoustic pixel resolution is also 2 cm. The dynamic range of working is 2 dB, may be higher. The camera has a picture resolution of 5 megapixel. The object is at a distance of 2 m to 20 m from the directional microphone, in other words the working range of the set up is between 2 to 20 m. Larger distances will require a larger dish of the directional microphone or will result in a larger acoustic pixel resolution. The frequency range of operation is between 30 to 50 kHz. These specifications only relate to one possible embodiment, however further exploration of possibilities and technologies might lead to better or broader specifications, and areas of use.

With the afore-mentioned specifications it is possible to make partial discharge emissions or high frequency acoustic waves visible in medium and high voltage systems. Because of the sensitivity and the ability to quantify small differences even discharges inside medium voltage air insulated switchgear will be visible under certain conditions.

This high frequency acoustic spectrum imaging is a powerful tool in the field of health monitoring and predictive analysis for medium and high voltage assets. This technology can be used for locating and quantifying partial discharges in high voltage applications. It can be applied to forecast the deterioration rates of medium and high voltage assets in order to set the proper strategy for their maintenance. The feedback from the field of view by detailed analysis can be used to set the correct indices for the condition of the medium and high voltage assets or equipments in asset management strategies.

But the use of high frequency acoustic spectrum imaging is not just limited to the above mentioned use, it can find application in several other fields too, for example for leak detection in pressurized air networks, for plotting acoustic images in urban areas such as football stadiums, train carriages etc., for detection of radio signals of mobile network, micro waves detection, and any other area where there is interest in the amplitude and frequency of sound in and beyond human hearing with a tendency to know exactly the origin or source of the sound waves.

The above-mentioned and other features of the invention will now be addressed with reference to the accompanying drawings of the present invention. The illustrated embodiments are intended to illustrate, but not limit the invention.

The drawings contain the following figures, in which like numbers refer to like parts, throughout the description and drawing.

Other features which are considered as characteristic for the invention are set forth in the appended claims.

Although the invention is illustrated and described herein as embodied in a high frequency acoustic spectrum imaging method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
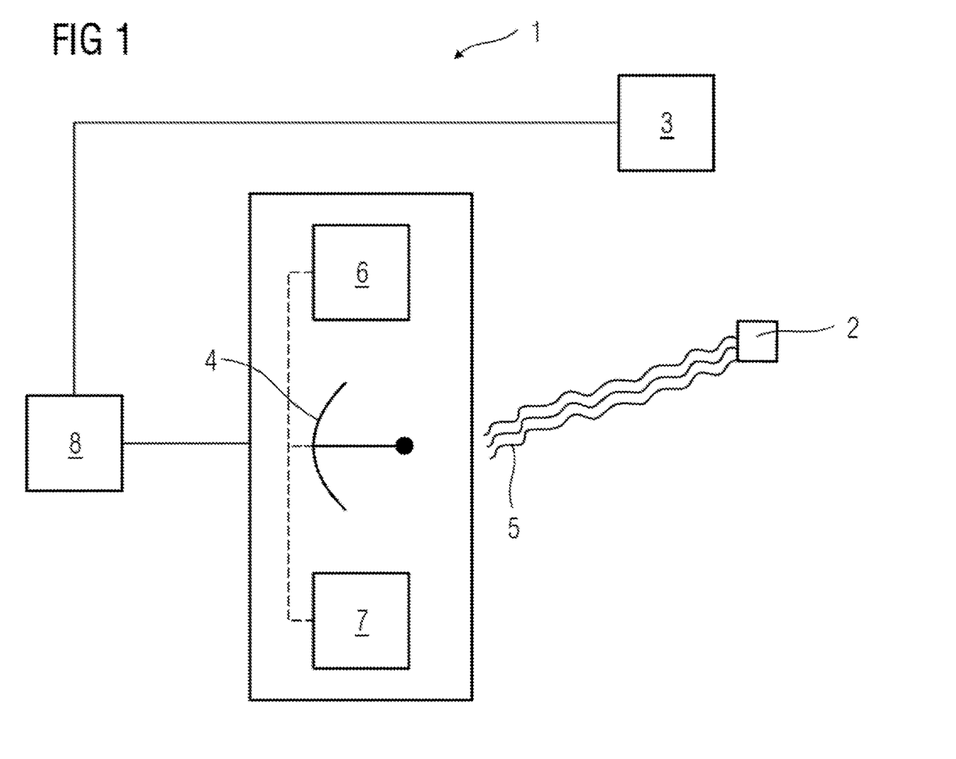
FIG. 1 is a schematic diagram showing a device for creating a high frequency acoustic spectrum image for an object.

Referring now to the figures of the drawing in detail and first, particularly, to FIG. 1 thereof, there is shown a device 1 for creating a high frequency acoustic spectrum image for an object 2. The image of the object 2 is captured by a camera 3. This image is equivalent to an ordinary photograph captured by a camera. It contains the object and its surrounding area that comes in the field of view of the camera. A directional microphone 4 scans the field of view to detect and pick up high frequency acoustic waves 5 emanating from the object 2.

A medium or a high voltage asset typically emits high frequency acoustic signals when its operational health is deteriorating. An example of such an asset that radiates high frequency acoustic signal when failing is a switch gear.

The directional microphone 4 after capturing the high frequency acoustic waves 5 sends a corresponding electrical signal to the microphone data processing unit 6 which generates a corresponding acoustic signal data dependent on the high frequency acoustic waves 5. This acoustic signal data is sent to a processor 8 for further processing.

A feedback unit 7 sends a real-time feedback position signal of coordinates (x, y) of focal point of the directional microphone 4 corresponding to the acoustic signal data to the processor 8. Therefore, for every measurement of the acoustic signal data there will be a corresponding coordinate (x, y) of the location of the directional microphone 4 which will identify the location on the image from where the high frequency acoustic waves 5 were coming and were subsequently picked up by the directional microphone 4.

The processor 8 plots a visual representation of the acoustic signal data mapping it to the coordinates (x, y) of the directional microphone 4 measured in respect of grids on a raster. The raster has grids and the location of the coordinates (x, y) is identified in respect of the grids on the raster. The processor 8 then superimposes the raster on the image of the object 2 in the field of view to create the high frequency acoustic spectrum image for the object 2.

Thus, the rasterized image of the object will contain the visual representation of the acoustic signal data which is then superimposed on the image 11 captured by the camera 3 to finally create the high frequency acoustic spectrum image 12 for the object 2.

The high frequency acoustic spectrum image for the object 2 can contain visual information in the form of color-code indicating the intensity or the strength of the high frequency acoustic waves 5 picked up by the directional microphone 4.

The microphone data processing unit 6 is connected with the feedback unit 7 to record the location or the coordinates (x, y) of the focal point of the directional microphone 4 with the help of sensors as well as record the acoustic signal data corresponding to the high frequency acoustic waves 5 emitted by the object 2.

Figure 2:
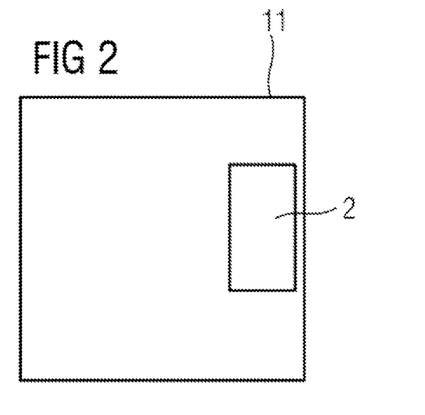
FIG. 2 depicts a sample image captured by the camera.

Referring now to FIG. 2, there is shown a sample image 11 that is captured by the camera 3 from the field of view. The image 11 captured contains the object 2 for which the acoustic spectrum image 12 is to be created. This object 2 can be a switch gear, a disconnector, a power line termination, a cable termination, an insulator, a bushing, a power transformer, a rectifier, a busbar or any other similar high and medium voltage asset. The image used is an ordinary photograph captured by a camera 3 with the object 2 and the area surrounding the object 2 which falls within the field of view of the camera 3 or the user.

Figure 3:
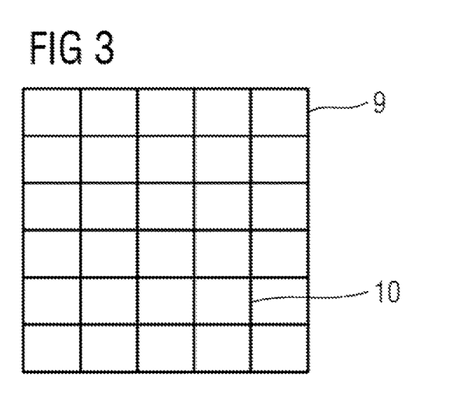
FIG. 3 depicts a sample raster created with grids as an overlay on the image.

FIG. 3 shows a sample raster 9 having grids 10. The grids 10 are arranged with a certain distance from the adjacent grids. The grid density can be 2 cm×2 cm for example. Any other suitable distance can be used too. But uniformly all grids 10 must be equidistant from the adjacent grids to form a uniform raster 9.

Figure 4:
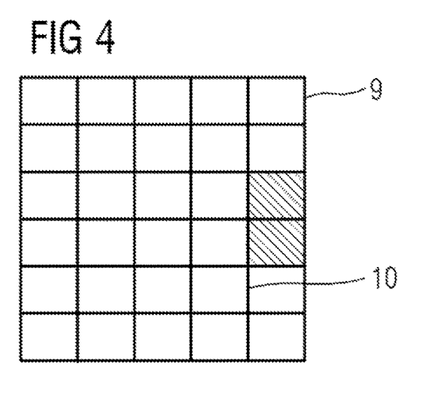
FIG. 4 shows the acoustic signal data plotted by the processor in accordance to the corresponding high frequency acoustic waves captured at the particular coordinates on the raster.

FIG. 4 shows the acoustic signal data plotted by the processor 8 in accordance to the corresponding high frequency acoustic waves 5 captured at the particular coordinates (x, y) on the raster 9. The raster 9 shown in FIG. 4 contains visual information about the acoustic signal data generated by the microphone data processing unit 6 based on the acoustic waves 5 captured by the microphone 4 while scanning the area of the field of view. This information is mapped to the corresponding location coordinates (x, y) of the focal point of the directional microphone 4 on the grid 10. This acoustic signal data contains important information about the amplitude and the main frequency of the high frequency acoustic waves 5. Every measurement of acoustic signal data generated has a corresponding coordinate (x, y) representing the location of the focal point of the directional microphone 4 which in turn identifies the location from where the acoustic waves 5 are emanating, in view of the raster 9.

Figure 5:
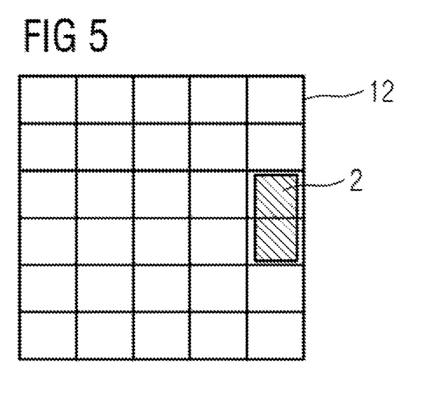
FIG. 5 shows a sample high frequency acoustic spectrum image created for an object by overlaying the rasterized image with acoustic signal data on the image captured by the camera.

FIG. 5 shows a sample high frequency acoustic spectrum image 12 for the object 2 created by superimposing the information filled raster 9, created as shown in FIG. 4, on the image 11 captured by the camera 3 as shown in FIG. 2. This final image 12 shows the objects 2 and the visual representation of the acoustic signal data, together mapped as one image 12.

Figure 6:
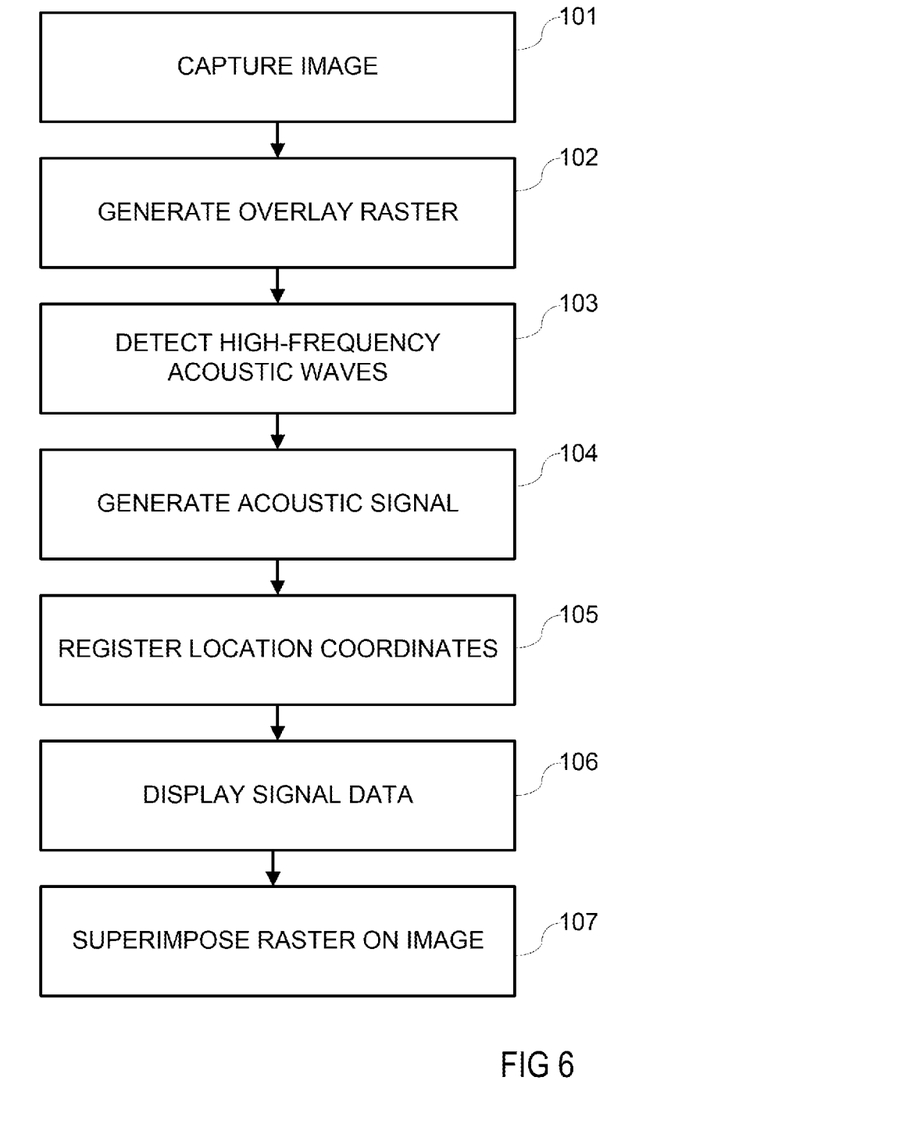
FIG. 6 shows a flowchart containing the steps according to the disclosed method.

FIG. 6 displays the method 100 comprising of steps to be carried out for creating a high frequency acoustic spectrum image 12 for an object 2 using the high frequency acoustic waves 5 that are emitted by the object 2 over a field of view captured by a camera 3. These high frequency acoustic waves 5 are picked up by a directional microphone 4 located at a certain distance from the object 2. This distance is the working range of the microphone, for example 2 to 20 metres. The rasterized image of the object 2 contains visual information about the high frequency acoustic waves 5 captured by the directional microphone 4.

The method 100, as seen in FIG. 6, comprises of a first step 101 of capturing an image 11 of the object 2 in the field of view. In the next step 102 a raster 9 is created with grids 10 as an overlay on the image 11. In the next step 103 the high frequency acoustic waves 5 emanating from the object 2 are detected corresponding to a grid 10 location identified by its coordinates (x, y) on the raster 9. The high frequency acoustic waves 5 are detected by scanning an area within the image 11 by moving the directional microphone 4 through the grids 10 of the raster 9. The method 100 further comprises a step 104 of generating an acoustic signal data corresponding to the high frequency acoustic waves 5 measured while scanning the field of view. In the next step 105 the coordinates (x, y) of focal point of the directional microphone 4 corresponding to every measurement of the acoustic signal data are registered. Once the coordinates (x, y) are available, the acoustic signal data is visually represented on the raster 9 corresponding to its respective coordinates (x, y) on the grids 10 of the raster 9 in the next step 106. In the final step 107 the raster 9 is superimposed on the captured image 11 to arrive at the high frequency acoustic spectrum image 12 for the object 2.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore contemplated that such modifications can be made without departing from the embodiments of the present invention as defined.

The invention claimed is:

1. A method for high frequency acoustic spectrum imaging for an object over a field of view, the method comprising:
   capturing an image of the object in the field of view;
   creating a raster with grids as an overlay on the image;
   detecting high frequency acoustic waves emanating from the object with a directional microphone by scanning through the grids of the raster;
   generating an acoustic signal data corresponding to the high frequency acoustic waves detected while scanning;
   registering coordinates of focal point of the directional microphone on the grid corresponding to each measurement of the acoustic signal data;
   plotting a visual representation of the acoustic signal data on the raster corresponding to its coordinates on the grid;
   superimposing the raster on the captured image to get the high frequency acoustic spectrum image for the object.

2. The method according to claim 1, wherein the directional microphone is a parabolic microphone.

3. The method according to claim 1, which comprises setting a grid density of the raster to be equivalent to a diameter or a circumference of a focal point of the directional microphone.

4. The method according to claim 1, wherein the acoustic signal data at each grid comprises one or both of the following:
   an amplitude of the high frequency acoustic wave;
   a main frequency of the high frequency acoustic wave.

5. The method according to claim 1, wherein the step of registering coordinates further comprises a step of sending a real-time feedback position signal of the coordinates to a processor.

6. The method according to claim 5, which comprises setting a minimum and a maximum amplitude threshold of the high frequency acoustic signal in the processor.

7. The method according to claim 4, wherein the high frequency acoustic spectrum image for the object further comprises a color-coded visual representation of the amplitude or the frequency of the acoustic signal data.

8. The method according to claim 7, wherein:
   when the amplitude of the high frequency acoustic wave received by the directional microphone lies above the maximum amplitude threshold, the high frequency acoustic spectrum image for the object visualizes a first colored area on the raster; and
   when the amplitude of the high frequency acoustic signal received by the directional microphone lies below the minimum amplitude threshold, the high frequency acoustic spectrum image for the object visualizes a second colored area on the raster.

9. The method according to claim 1, which comprises registering the coordinates using a device selected from the group consisting of an analog movement sensor, a servomotor, a joystick, and a unit for tracking a laser.

10. The method according to claim 1, wherein the object is any one of a switch gear, a disconnector, a power line termination, a cable termination, an insulator, a bushing, a power transformer, a rectifier or a busbar.

11. The method according to claim 1, wherein the high frequency acoustic spectrum image for the object contains amplitude or frequency representation alternatively based on an input given by a user.

12. A device for generating a high frequency acoustic spectrum image of an object, the device comprising:
   a camera for taking an image of the object;
   a directional microphone for receiving high frequency acoustic waves emanating from the object;
   a microphone data processing unit connected to said microphone for generating an acoustic signal data corresponding to the high frequency acoustic waves;
   a feedback unit connected to said microphone for sending to a processor a real-time feedback position signal of coordinates of a focal point of the directional microphone corresponding to the acoustic signal data;
   said processor being configured for plotting a visual representation of the acoustic signal data mapped to the corresponding coordinates on a raster and superimposing the raster on the image to create the high frequency acoustic spectrum image for the object.

13. The device according to claim 12, wherein said feedback unit comprises a device selected from the group consisting of an analog movement sensor, a servomotor, a joystick, and a unit for tracking a laser.

14. The device according to claim 12, wherein the acoustic signal data comprises one or both of the following:

an amplitude of the high frequency acoustic wave;
a main frequency of the high frequency acoustic wave.

15. The device according to claim 12, wherein the object is a device selected from the group consisting of a switchgear, a disconnector, a power line termination, a cable termination, an insulator, a bushing, a power transformer, a rectifier, and a busbar.

16. The device according to claim 12, wherein the high frequency acoustic spectrum image for the object further comprises a color-coded visual representation of the acoustic signal data signifying intensity of the high frequency acoustic waves.

\* \* \* \* \*